United States Patent [19]

Pines et al.

[11] Patent Number: 5,449,678

[45] Date of Patent: Sep. 12, 1995

[54] ANTI-FIBROTIC QUINAZOLINONE-CONTAINING COMPOSITIONS AND METHODS FOR THE USE THEREOF

[75] Inventors: Mark Pines, Rehovot; Arnon Nagler, Jerusalem; Shimon Slavin, Jerusalem, all of Israel

[73] Assignees: Agricultural Research Organization, Minstry of Agriculture; Hadasit Medical Research Services & Development Company Ltd., both of Israel

[21] Appl. No.: 181,066

[22] Filed: Jan. 14, 1994

[51] Int. Cl.[6] .......................................... A61K 31/505
[52] U.S. Cl. ............................................ 514/259
[58] Field of Search ................................. 514/259

[56] References Cited

U.S. PATENT DOCUMENTS 3,320,124  5/1967  Waletzky .................... 167/53

OTHER PUBLICATIONS

Granot et al., Biochim. Biophys. Acta, 1156(2), 107–112. 1993.

Primary Examiner—Marianne M. Cintins
Assistant Examiner—Phyllis G. Spivack
Attorney, Agent, or Firm—Popham, Haik, Schnobrich & Kaufman, Ltd.

[57] ABSTRACT

The invention provides an anti-fibrotic composition, comprising an amount of a compound of formula I:

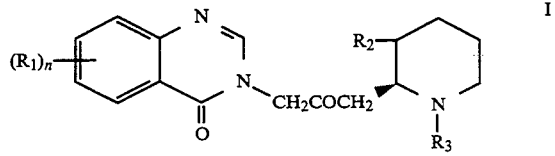

wherein:
  n=1 or 2
  $R_1$ is a member of the group consisting of hydrogen, halogen, nitro, benzo, lower alkyl, phenyl and lower alkoxy;
  $R_2$ is a member of the group consisting of hydroxy, acetoxy, and lower alkoxy, and
  $R_3$ is a member of the group consisting of hydrogen and lower alkenoxy-carbonyl;

effective to inhibit collagen type I synthesis as active ingredient therein.

6 Claims, 10 Drawing Sheets

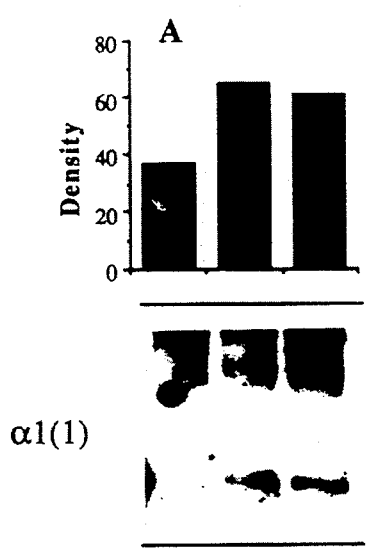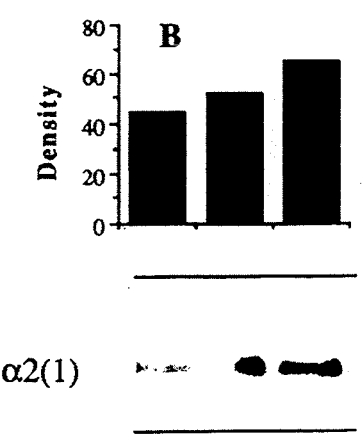
FIG. 4A
FIG. 4B

ANTI-FIBROTIC QUINAZOLINONE-CONTAINING COMPOSITIONS AND METHODS FOR THE USE THEREOF

The present invention relates to compositions containing quinazolinones. More particularly, the present invention relates to an anti-fibrotic composition comprising an amount of quinazolinone derivative as herein defined, effective to inhibit collagen type I synthesis, which is therefore useful as a pharmaceutical, as well as a cosmetic, composition for a multitude of conditions, as described and discussed hereinbelow.

In. U.S. Pat. No. 3,320,124, issued in 1967, there is described and claimed a method for treating coccidiosis with quinazolinone derivatives.

Halofuginone, otherwise known as 7-bromo-6-chloro-3-[3-(3-hydroxy-2-piperidinyl)-2-oxopropyl]-4(3H)-quinazolinone, was first described and claimed in said patent by American Cyanamid Company, and was the preferred compound taught by said patent and the one commercialized from among the derivatives described and claimed therein.

Subsequently, U.S. Pat. Nos. 26,833 and 4,824,847; 4,855,299; 4,861,758 and 5,215,993 all relate to the coccidiocidal properties of halofuginone, while U.S. Pat. No. 4,340,596 teaches that it can also be used for combatting theileriosis.

In 1991, one of the present inventors published an article reporting that reduced collagen synthesis was noted and identified as an important causitive factor in the skin tearing and reduced skin strength of fowl treated with halofuginone, administered in the amounts recommended for use as a coccidiostat. It was also found that, at the cellular level, halofuginone suppressed collagen synthesis by avian skin fibroblasts [I. Granot, et al., *Poult. Sci.*, Vol. 70, pp. 1559–1563 (1991)].

At that time, however, it was neither taught, recognized or suspected that halofuginone or the related quinazolinone derivatives taught in U.S. Pat. No. 3,320,124 could be effectively used for treatment of fibrotic diseases and for related cosmetic applications, and for good reason.

Clinical conditions and disorders associated with primary or secondary fibrosis, such as systemic sclerosis, graft-versus-host disease (GVHD), pulmonary and hepatic fibrosis and a large variety of autoimmune disorders, are distinguished by excessive production of connective tissue, resulting in destruction of normal tissue architecture and function. These diseases can best be interpreted in terms of perturbations in cellular functions, a major manifestation of which is excessive collagen deposition.

It is generally recognized that at present, most treatments of fibrotic diseases are ineffective and have little effect upon their inexorable pathological progression. Various attempts have been made in order to reduce collagen deposition in the extracellular space. As is known, progressive fibro- proliferative diseases exhibit excessive production of connective tissues, which results in destruction of normal tissue architecture and function. The crucial role of collagen in fibrosis has prompted attempts to develop drugs that inhibit its accumulation [K. I. Kivirikko, *Annals of Medicine*, Vol. 25, pp. 113–126 (1993)].

Such drugs can act by modulating the synthesis of the procollagen polypeptide chains, or inhibit some specific post-translational events, which will lead either to reduced formation of extra-cellular collagen fibers or to an accumulation of fibers with altered properties. Only a few inhibitors of collagen synthesis are available, despite the importance of this protein in sustaining tissue integrity and its involvement in various disorders.

Cytotoxic drugs have been used in an attempt to slow collagen-producing fibroblast proliferation [J. A. Casas, et al., *Ann. Rhem. Dis.*, Vol. 46, p. 763 (1987)], among them colchicine, which slows collagen secretion into the extracellular matrix [D. Kershenobich, et al., *N. Engl. J. Med.*, Vol. 318, p. 1709 (1988)] and inhibitors of key collagen metabolism enzymes [K. Karvonen, et al., *J. Biol. Chem.*, Vol. 265, p. 8415 (1990); and C. J. Cunliffe, et al., *J. Med. Chem.*, Vol. 35, p. 2652 (1992)].

Unfortunately, none of these inhibitors are collagen-type specific. Also, there are serious concerns about toxic consequences of interfering with biosynthesis of other vital collagenous molecules, such as Clq in the classical complement pathway, acetylcholine esterase of the neuromuscular junction endplate, conglutinin and pulmonary surfactant apoprotein.

Other drugs which can inhibit collagen synthesis, such as nifedipine and phenytoin, inhibit synthesis of other proteins, as well, therefore blocking the collagen biosynthetic pathway non-specifically [T. Salo, et al., *J. Oral Pathol. Med.*, Vol. 19, p. 404 (1990)].

Collagen cross-linking inhibitors such as β-aminopropionitrile are also non-specific although they can serve as useful antifibrotic agents. Their prolonged use causes lathritic syndrome and interferes with elastogenesis, since elastin, another fibrous connective tissue protein, is also cross-linked. In addition, the collagen cross-linking inhibitory effect is secondary, and collagen overproduction has to precede its degradation by collagenase.

According to the present invention, it has now been discovered that halofuginone, on the other hand, is a specific α1 type I collagen synthesis inhibitor. Its specificity resides in its mode of action: inhibition of collager α1 (I) promoter. On the morphological level, halofuginone decreased the fibrosis by decreasing collagen type I synthesis, and prevented collagen deposition and the replacement and disappearance of the subcutaneous fat tissue, all of which are characteristic of mice afflicted with chronic GVHD.

It is therefore also believed that the other quinazolinone derivatives described and claimed in U.S. Pat. No. 3,320,124 the teachings of which are incorporated herein by reference, have similar properties.

Thus, according to the present invention, there is now provided an anti-fibrotic composition, comprising an amount of a compound of formula I:

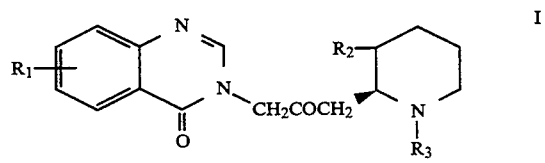

wherein:
R₁ is a member of the group consisting of hydrogen, halogen, nitro, benzo, lower alkyl, phenyl and lower alkoxy;
R₂ is a member of the group consisting of hydroxy, acetoxy, and lower alkoxy, and $R_3$ is a member of the group consisting of hydrogen and lower alkenoxy-carbonyl;

effective to inhibit collagen type I synthesis as active ingredient therein.

According to the present invention, there are now provided compositions for treating or preventing the following disorders and related conditions:

1) diseases caused by, or associated with, excessive collagen type I deposits or fibrosis, including primary or secondary diffuse, local, focal, or organ-specific fibrosis following inflammation in a variety of auto-immune and inflammatory disorders (i.e., autoimmune and degenerative arthritis, liver cirrhosis due to alcohol or chronic active hepatitis, systemic lupus erythematosis, SLE, Sjogren syndrome, and diffuse systemic sclerosis with scleroderma, primary and secondary pulmonary and broncho-alveolar fibrosis, fibrous dysplasia, cystic fibrosis, myelosclerosis, etc.;

2) fibrosis around foreign bodies (i.e., mechanical implants: artificial pancreas devices with insulin or insulin-secreting islets; artificial valves; artificial blood vessels, silicon implants, etc.;

3) systemic, organ or site-specific fibrosis post-irradiation, fibrosis secondary to chronic inflammatory disorders and cytotoxic agents;

4) scar formation and/or intimal thickening due to surgical vascular interventions (i.e., coronary artery bypass, vascular surgery and artificial vascular implants);

5) cutaneous, ocular and mucosal superficial or deep and destructive fibrosis and/or scar formation due to systemic diseases, infections (i.e., acne vulgaris, trachoma, etc.) or burns, ionizing irradiation, or other physico-chemical trauma;

6) chronic graft vs host disease following allogeneic bone marrow transplantation with secondary local, organ-specific or systemic fibrosis and/or scleroderma, and 7) scar formation following surgical incisions and cosmetic surgical interventions.

Fibrotic processes are the primary cause or the end result of the healing process of multiple inflammatory, physical injuries and autoimmune disorders, as well as aging. No specific inhibitor of collagen synthesis is available to date. Some known inhibitors of collagen synthesis are non-selective inhibitors of protein synthesis, while others are not specific to collagen type. Halofuginone, and assumedly also the other related above-defined compounds of formula I, specifically inhibit collagen type I synthesis, without affecting proliferation of cells or synthesis of any other proteins through specific inhibition of collagen type I, by specific binding to the promoter of collagen type I gene. Hence, for the first time, specific anti-collagen agents are available for clinical practice, and these agents will be discussed and exemplified hereinafter with relation to halofuginone, which is the preferred compound for use in the present invention. As a specific collagen type I inhibitor, halofuginone has a broad spectrum of potential clinical applications, theoretically with minimal toxicity. Halofuginone is a simple chemical compound with low molecular weight, and so may be readily absorbed orally or applied topically.

The extremely low concentrations of halofuginone needed to inhibit collagen type I synthesis at transcriptional level, regardless of tissue or animal species, permission by the U.S. Food and Drug Administration (FDA) for its use in edible farm animals, and its effects on skin collagen content at concentrations which do not affect body growth, make halofuginone the first truly promising clinically useful anti-fibrotic drug.

Furthermore, topical compositions to prevent cutaneous, ocular and mucosal scar formation and for clinical application for cosmetic purposes are also provided by the present invention.

Collagen molecules are an integral part of fibrosis elements or supramolecular structures in extracellular spaces, which function as major components of various connective tissues. Of 13 distinct collagen types, representing at least 21 individual gene products, skin contains especially type I (85%) and type III (15%) collagen. Three representative major clinical conditions associated with fibrosis as a major pathogenesis of the disease are described below:

a) Primary or secondary systemic sclerosis (scleroderma): A chronic disorder, characterized by fibrotic and inflammatory changes in skin and internal organs [E. C. Leroy, *Coll. Relat. Res.*, Vol. 1, p. 301 (1981)]. It is approximately 10 times more prevalent than the incidence, at approximately 100 per million in the population. [T. A. Medsger, in C. M. Black and A. R. Myers (eds.), *Systemic Sclerosis (Scleroderma)*, Gower Medical, New York, U.S.A. (1985)] and in some cases up to 290 per million [H. R. Maricq, et al., *Arthritis Rhem.*, Vol. 32, p. 998 (1989)]. Its etiology and pathogenesis are not fully understood, but autoimmunity is thought to be involved in microvascular modifications and excessive fibroblastic activity with abnormal collagen deposits, which are constant features of scleroderma. Skin biopsies of scleroderma patients exhibited elevated levels of collagen type I gene expression [K. Herrmann, et al., *J. Invest. Dermatol.*, Vol. 97, p. 219 (1991)] and fibroblasts recovered from these patients revealed increased synthesis of collagen and fibronectin [E. C. Leroy, *J. Clin. Invest.*, Vol. 54, p. 880 (1974)]. Skin and subcutaneous tissues mainly are involved; this involvement can extend to tendons and muscles. Various internal organs can be affected (blood vessels, gastro-intestinal tract, lungs, heart, kidneys). Cutaneous and/or systemic sclerosis, indistinguishable from primary scleroderma, may complicate chronic graft vs host disease, following allogeneic bone marrow transplantation, which supports the autoimmune etiology of the primary disease.

b) Pulmonary fibrosis

Interstitial lung diseases are heterogenous disorders, characterised by diffuse involvement of lung parenchyma ]R. G. Crystal et al., *Am. J. Med.*, Vol. 70 pp 542–568 (1981)], mostly progressive and often fatal. The most common etiology includes chronic inhalation of dusts containing silica, as in miners and asbestos workers. Pulmonary fibrosis or broncho-alveolar fibrosis may be primary or secondary to bone marrow transplantation due to radiation, high dose chemotherapy, infectious complications, or associated with immune or autoimmune etiology. Pulmonary fibrosis may also result from chemotherapy or paraquat poisoning. In most cases, abnormally high levels of collagen type I synthesis were observed [S. M. Krane, in K. A. Picz and A. H. Reddi (eds.), *Extracellular Matrix Biochemistry*, Elsevier, New York, U.S.A. (1984)].

c) Hepatic fibrosis

Increased hepatic connective tissue is relatively common. Depending on its extent and distribution, hepatic fibrosis may be either of little clinical consequence or devastating, fatal cirrhosis. Major etiologies of hepatic fibrosis in the West include alcoholic-nutritional diseases, viral hepatitis, and autoimmune etiology (i.e., secondary to chronic active hepatitis or primary biliary cirrhosis). Other underlying diseases are iron overload, copper metabolism disorders, extra hepatic biliary obstruction, primary biliary cirrhosis and chronic congestive heat failure. Another important cause in millions worldwide is hepatic chistosomiasis. Excessive production of collagen is usual in liver fibrosis, although the pattern of collagen deposition may be distinctive for each disease.

In addition to the above, there are many other possible clinical indications, in which the prevention of collagen type I associated fibrosis is desired, and which can now be treated with the compositions of the present invention.

Thus, the present invention provides compositions and methods for:

1) inhibition of collagen deposition in cirrhosis, including primary billiary cirrhosis as well as alcoholic and post-hepatitic cirrhosis, and cirrhosis due to iron overload copper metabolism disorders, extra hepatic billiary obstructions and chistosomiasis;
2) inhibition of collagen synthesis as a treatment for scleroderma;
3) inhibition of collagen synthesis as a treatment for chronic graft-versus-host disease;
4) inhibition of collagen synthesis as treatment of keloid and hypertrophic scar formations following trauma and surgery;
5) use in cosmetic applications to reduce scar formation and collagen deposition for preventing of the aging process of the skin;
6) inhibition of collagen synthesis as a treatment for myelofibrosis, including idiopathic myelofibrosis, and myelofibrosis in myeloproliferative disorders;
7) inhibition of increased collagen synthesis in dermatology disorders, such as buleous pemphigoid, erysipelas, erythema multiforme, hydroa vicciniforme, acne keloidalis;
8) inhibition of collagen synthesis for treatment of lung fibrosis, including autoimmune lung disease, idiopathic fibrosis, post-inflammatory fibrosis, vasculitis, radiation and chemotherapy-induced fibrosis, fibrosis as part of interstitial pneumonitis;
9) inhibition of fibrosis in diseases of the musculo-skeletal system, including arthritis and tendenitis, bursitis and frozen shoulder;
10) inhibition of post-surgery scar formation, including heart surgery, plastic surgery, vascular surgery, orthopedic surgery and opthalmologic surgery, including filtration operation for glaucoma;
11) inhibition of collagen synthesis as a treatment for scar formations post burns, ionizing irradiation, or other physico-chemical trauma;
12) inhibition of fibrosis due to foreign body reactions, including artificial implants such as artificial pancreas, artificial hip or other joints, anastomosis in heart aorta and other microvascular surgery or artificial valves;
13) inhibition of fibrosis as the end process of autoimmune disease, including fibrosis in the kidneys in systemic lupus erythermatosis, fibrosis in lung in autoimmune disease of the lung; fibrosis of the liver post chronic active hepatitus; autoimmune diseases of the eyes such as uveitis, or of the oral and salivary glands, such as Sjogren's syndrome, and autoimmune-induced arthritis;
14) treatment of post-inflammatory fibrosis, such as myocardial fibrosis, post-Coxsackievirus B viral disease, or bacterial endocarditis; post-inflammatory fibrosis of the pleura, and
15) treatment of CNS lesions due to primary or secondary fibrosis, such as glial scar formation or amyotropic lateral sclerosis.

The compositions of the present invention may be administered by any means that provide anti-fibrotic and/or collagen type I synthesis inhibitory activity. For example, administration may be parenteral, subcutaneous, intravenous, intramuscular, intratecal, oral, or topical.

While it is possible for the active ingredients to be administered alone, it is preferable to present them as pharmaceutical formulations. The formulations of the present invention comprise at least one active ingredient, as above defined, together with one or more acceptable carriers therefor and, optionally, other therapeutic ingredients. The carrier(s) must be acceptable in the sense of being compatible with the other ingredients of the formulation, and not deleterious to the recipient thereof.

The formulations may conveniently be presented in unit dosage form, and may be prepared by any of the methods well-known in the art of pharmacy. Such methods include the step of bringing into association the active ingredient with the carrier, which constitutes one or more accessory ingredients. In general, the formulations are prepared by uniformly and intimately bringing into association the active ingredient with liquid carriers or finely-divided solid carriers, or both, and then, if necessary, shaping the product.

The dosage of active ingredients in the composition of this invention may be varied; however, it is necessary that the amount of the active ingredient shall be such that a suitable dosage form is obtained. The selected dosage form depends upon the desired therapeutic or cosmetic effect, on the route of administration, and on the duration of the treatment.

Administration dosage and frequency will depend on the age and general health condition of the patient, taking into consideration the possibility of side effects. Administration will also be dependent on concurrent treatment with other drugs and the patient's tolerance of the administered drug.

Solid dosage forms for oral administration include capsules, tablets, pills, powders and granules. In such solid dosage forms, the active compound is admixed with at least one inert diluent, such as sucrose, lactose or starch. Such dosage forms can also comprise, as is normal practice, additional substances other than inert diluent. In the case of capsules, tablets and pills, the dosage forms may also comprise buffering agents. Tablets and pills can additionally be prepared with an enteric coating.

Liquid dosage forms for oral administration include pharmaceutically acceptable emulsions, solutions, suspensions, syrups and elixirs, containing inert diluents commonly used in the pharmaceutical art. Besides inert diluents, such compositions can also include adjuvants, such as wetting agents, emulsifying and suspending agents, and sweeteners.

Preparations according to the present invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters, such as ethyl oleate.

Topical administration can be effected by any method commonly known to those skilled in the art and include, but is not limited to, incorporation of the composition into creams, ointments, or transdermal patches.

When formulated in a cream, the active ingredients may be employed with an oil-in-water cream base.

If desired, the aqueous phase of the cream base may include, for example, at least 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of the present invention may be constituted from known ingredients in a known manner. While the phase may comprise merely an emulsifier (otherwise known as an emulgent), it desirably comprises a mixture of at least one emulsifier with a fat or an oil, or with both a fat and an oil. Preferably, a hydrophilic emulsifier is included, together with a lipophilic emulsifier, which acts as a stabilizer. It is also preferred to include both an oil and a fat. Together, the emulsifier(s), with or without stabilizer(s), make up the so-called emulsifying wax, and the wax, together with the oil and/or fat, make up the so-called emulsifying ointment base, which forms the oily dispersed phase of the cream formulations.

Emulgents and emulsion stabilizers suitable for use in the formulation of the present invention include Tween 60, Span 80, cetostearyl alcohol, myristyl alcohol, glyceryl mono-stearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester or coconut fatty acids, isopropyl myristate, decyl oleate, isopropyl palmitate, butyl stearate, 2-ethylhexyl palmitate, or a blend of branched chain esters known as Crodamol CAP may be used, the last three being preferred esters. These may be used alone or in combination, depending on the properties required. Alternatively, high melting-point lipids, such as white soft paraffin and/or liquid paraffin, or other mineral oils can be used.

The compositions of the present invention might be applied locally, not only topically but also in slow-release devices in association with artificial implants (i.e., artificial pancreas, musculo-skeletal devices, etc.) as well as surgical sutures, absorbable patches for use in surgery, etc.

While the invention will now be described in connection with certain preferred embodiments in the following examples and with reference to the appended figures, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 3 shows immunoprecipitation of collagen type I from avian skin fibroblast cultures;

FIG. 4 graphically shows the effect of halofuginone on type I procollagen gene expression;

FIG. 6 shows the effect of halofuginone on $\alpha 1$ and $\alpha 2$ collagen type I and collagen type II gene expression in avian epiphyseal growth-plate chondrocytes;

FIG. 16 shows the effect of halofuginone on skin morphology and collagen type I levels of control and GVHD mice.

EXAMPLE 1

Figure 1:
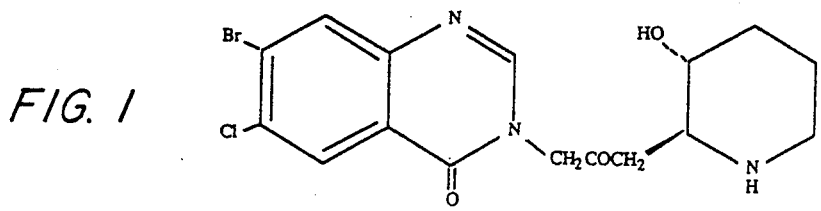
FIG. 1 shows the molecular structure of halofuginone.
Figure 2A:
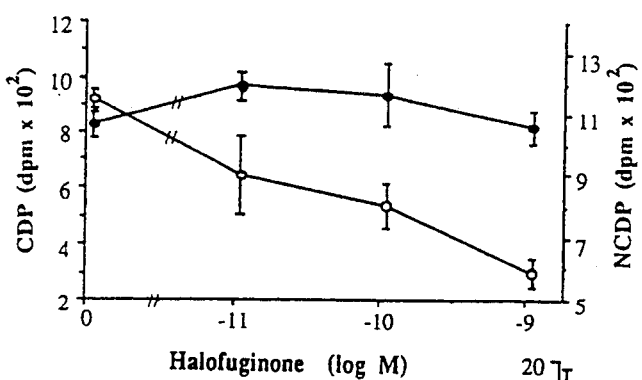
FIG. 2 graphically shows the effect of halofuginone on [$^3$H]proline incorporation into CDP and NCDP exported by avian skin fibroblasts of rat-1 cells, mouse skin fibroblasts and avian growth plate chondrocytes.
Figure 2B:
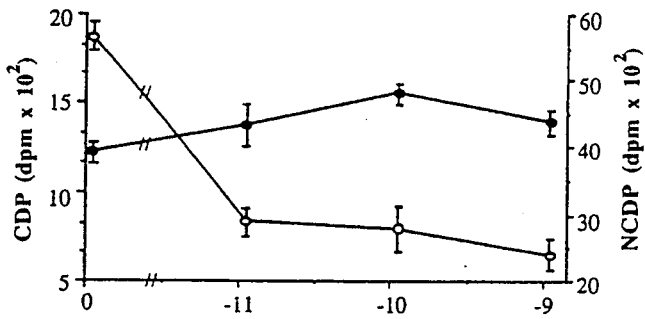
Figure 2C:
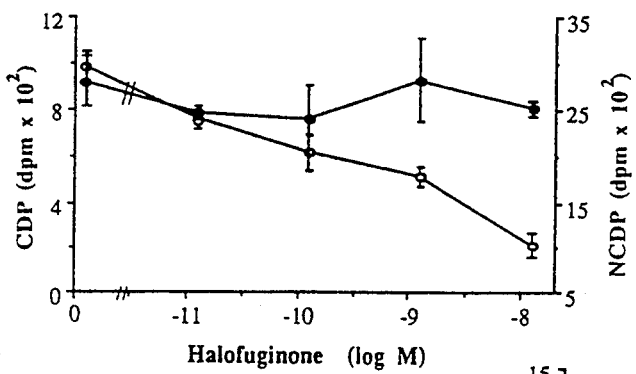
Figure 2D:
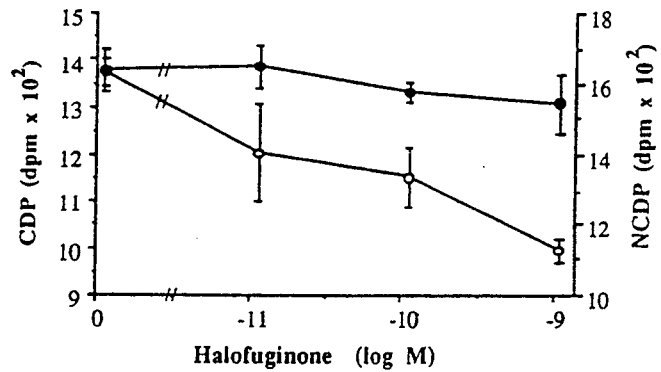

The effect of halofuginone on collagen type I gene expression and proline incorporation into collagenase-digestible proteins in avian skin fibroblasts was evaluated. The degradation pathway was evaluated by determining the extracellular collagen degradation. In order to assess collagen type, tissue and species specificity, primary cultures of avian and mammalian skin fibroblasts, avian epiphyseal growth plate chondrocytes and a rat embryo cell line which produce and secrete collagen type I, were used.

Materials and Methods

Materials

L-[2,3,4,5-$^3$H]proline (122 Ci/mmol) and L-[$^{35}$S]methionine (1186 Ci/mmol) were obtained from The Radiochemical Centre (Amersham, U.K.). Highly purified Clostridium histolyticum collagenase type VII free of non-specific proteinases, β-aminopropionitrile Dulbecco's modified Eagle's medium (DMEM) and trypsin-EDTA solution (0.25%–0.02%) were obtained from Sigma (St. Louis, Mo., U.S.A.). Fetal calf serum (FCS) was obtained from Biochemical Industries (Bet HaEmek, Israel). Specific antiserum for avian collagen type I was obtained from Institute Pasteur de Lyon, France. The probes pBSCA11 and pCAL2, containing inserts sequences corresponding to the mRNAs for chicken α1 and α2 procollagen type I chains respectively, and pBSCA12 containing an 890 bp fragment of type II collagen genomic DNA [E. I. Vuorio, et al., *Acta Chem. Scand.*, Vol. B38, pp. 237–241 (1984); and H. D. Nah, et al., *Collagen Rel. Res.*, Vol. 8, pp. 277–294 (1988)] were generously provided by Dr. W. B. Upholt, The University of Connecticut Health Center, Farmington, Conn., U.S.A. Halofuginone bromhydrate (Stenorol) was obtained from Roussell (Paris, France).

Cell Cultures

Avian skin fibroblasts and epiphyseal growth-plate chondrocytes from 2–4-week-old Leghorn X New Hampshire chickens were cultured as detailed previously [M. Pines, et al., *Endocrinology*, Vol. 23, pp. 360–365 (1988); and M. Pines, et al., *J. Endocrinol.*, Vol. 120, pp. 319–324 (1989)]. The transparent zone of the growth-plate (for cartilage cells) and slices of mouse (FVB/N) and chicken skin (for fibroblasts) were removed and incubated with 2 mg/ml collagenase. Cells were released from the tissue by forceful passages through a plastic pipette. The suspension was centrifuged and the pellet was resuspended in DMEM containing 5% FCS and plated in culture flasks. Only early passages (3–5) of the cells were used. Rat-1 cell line was cultured in DMEM containing 5% FCS [B. Steinberg, et al., *Cell*, Vol. 13, pp. 19–32 (1978)]. For the experiments, cells were detached by incubation with trypsin-EDTA medium, centrifuged, resuspended in DMEM with 5% FCS, plated in 1-ml wells, and then allowed to resume development for 1–3 days. Direct estimation of cell number was made by a cell counter (Coulter Electronics, Luton, U.K.).

Evaluation of Collagen and Non-Collagen Protein Synthesis

Cells were incubated with various concentrations of halofuginone in 0.5 ml glutamine-free DMEM containing 5% FCS, ascorbic acid (50 μg/ml), β-aminopropionitrile (50 μg/ml) and 2 μCi of [$^3$H]proline. At the end of incubation, the medium was decanted and incubated with or without collagenase for 18 h, followed by TCA precipitation [M. Pines, et al., *Bone Min.*, Vol. 9, pp. 23–33 (1990)]. The amount of radiolabeled collagen was estimated as the difference between total proline [$^3$H]-containing proteins in the sample incubated without the enzyme and those left after collagenase digestion [B. Peterkofsky, et al., *Biochemistry*, Vol. 10, pp. 988–994 (1971)].

Immunoprecipitation of Collagen Type I

Chicken fibroblasts were preincubated for 2 h with 1.5 ml methionine-free DMEM containing ascorbic acid (50 μg/ml), β-aminopropionitrile (50 μg/ml) and 5% dialyzed FCS. The media were then replaced with fresh media containing 10 μCi [$^{35}$S]methionine with or without $10^{-9}$M halofuginone for an additional 24 h. An aliquot of the medium was then incubated with or without collagenase for 18 h. At the end of the incubation, 4 μl of anti-avian collagen type I antiserum was added to the samples for an additional 2 h at 4° C. followed by precipitation with protein A-containing membranes prepared from *Staphylococcus aureus*. The pellet was dissolved in Tris-buffer containing 10% SDS, boiled, and subjected to 7.0% SDS polyacrylamide gel electrophoresis. The gels were treated with 50% acetic acid and 25% ethanol solution (18 h), followed by 2.5 h of treatment with 20% 2,5-diphenyloxazole (PPO) in dimethyl sulfoxide, then dried and autoradiographed.

Evaluation of Collagen Degradation

Cells were incubated for 24 h with various halofuginone concentrations. At the end of incubation, the media alone were reincubated for an additional 24 h period (at 1:1 dilution) with labeled proteins previously prepared by incubating fibroblasts with 15 μCi [$^3$H]proline/ml for 48 h. At the end of reincubation, the amount of radiolabeled collagenase-digestible proteins (CDP) remaining in the medium was determined as above. Collagen degradation was defined as the difference between the initial and final (after collagenase digestion) labeled CDP in the medium, over the initial concentration [I. Granot, et al., *Mol. Cell. Endrocinol.*, Vol. 80, pp. 1–9 (1991)].

RNA Isolation and Northern Blot Analysis

Total RNA was extracted by the acid-guanidinium-phenol-chloroform method [P. Chomczynski, et al., *Anal. Biochem.*, Vol. 162, pp. 156–159 (1987)]. The sample (20 μg) was subjected to electrophoresis through a 1% agarose gel containing 6% formaldehyde as described previously [O. Halevy, et al., *Mol. Cell. Endorcrinol.*, Vol. 75, pp. 229–235 (1991)]. The RNA was then blotted onto GeneScreen Plus membrane (New England Nuclear, Boston, Mass., U.S.A.) and hybridization with specific probes was carried out at 42° C. in buffer containing 50% formamide, 5×STE, 1% SDS, 1×Denhardt's solution, and 20 mM sodium phosphate (pH 6.8). The filters were washed according to the manufacturer's protocol, followed by autoradiography, and the intensity of the bands was quantitated by densitometry. The molecular weight of the mRNAs was estimated from the mobility of 28S (5.3 kb) and 18S (2.1 kb) RNA.

Results

Effect of Halofuginone on Collagen Export

The effect of halofuginone (FIG. 1) on collagen metabolism was evaluated in primary cultures of mouse and avian skin fibroblasts, an established rat fibroblast cell line (Rat-1) and primary cultures of avian epiphyseal chondrocytes. All types of cells cultured for 24 h in the presence of [$^3$H]proline, exported radiolabeled proteins into the medium, of which 30–60% were collagenase-digestible (CDP) and the remaining were, by definition, non-collagenase-digestible proteins (NCDP). In all cell cultures tested, halofuginone induced a dose-dependent inhibition of radiolabeled proline incorporation into CDP without affecting the appearance of

[$^3$H]proline in NCDP (FIG. 2). A concentration as low as $10^{-11}$M of halofuginone caused a reduction of 30%, 23%, and 24% in exported radiolabeled collagen in avian skin fibroblasts (FIG. 2A), mouse skin fibroblasts (FIG. 2C) and avian chondrocytes (FIG. 2D), respectively. Maximum inhibition was achieved with $10^{-9}$M to $10^{-8}$M of the drug. In Rat-1, the embryo cell line, $10^{-11}$M of halofuginone causes 65% reduction in the exported radiolabeled collagen (FIG. 2B).

Electrophoresis of the radiolabeled proteins, secreted by avian skin fibroblasts and subjected to immunoprecipitation with anti-avian collagen type I antiserum, revealed two major bands corresponding to $\alpha 1$ and $\alpha 2$ polypeptides of collagen type I. Of the other precipitated radiolabeled proteins, all except one were collagen-related, since they were collagenase-digestible (FIG. 3, left panel). Immunoprecipitation of the secreted radiolabeled proteins of cells incubated for 24 h with $10^{-9}$M halofuginone revealed reduction in both $\alpha 1$ and $\alpha 2$ polypeptides of collagen type I (FIG. 3, right panel).

Effect of Halofuginone on Cell Proliferation

Fibroblasts and chondrocytes were incubated with various concentrations of halofuginone for 24 h. Results (Table 1) show that cell proliferation was not affected significantly in any of the cell types tested, at concentrations of halofuginone which had caused a maximal reduction in exported radiolabeled collagen.

TABLE 1

Effect of halofuginone on cell proliferation
Cells were incubated with various halofuginone concentrations for 24 h in glutamin-free DMEM containing 5% FCS. At the end of the incubation, the medium was removed and the cells were detached with a trypsin-EDTA solution and counted in a cell counter. Each value is the mean ± SE of four wells.

| Additive (M) | Avian fibroblasts | Rat-1 (Cells × $10^3$) | Mouse fibroblasts | Chondrocytes |
|---|---|---|---|---|
| None | 146.2 ± 1.9 | 254.5 ± 15.0 | 126.2 ± 9.1 | 100.1 ± 8.0 |
| Halofuginone, $10^{-11}$ | 129.5 ± 3.0 | 273.7 ± 8.0 | 149.7 ± 14.6 | 101.5 ± 2.7 |
| $10^{-10}$ | 127.5 ± 7.1 | 272.2 ± 16.5 | 139.8 ± 25.0 | 97.6 ± 5.0 |
| $5 \times 10^{-10}$ | — | 265.6 ± 13.7 | — | 96.5 ± 1.6 |
| $10^{-9}$ | 146.8 ± 9.6 | 235.7 ± 5.4 | 135.7 ± 9.4 | |

Effect Of Halofuginone on Type I Collagen Gene Expression in Fibroblasts

The possibility that halofuginone modulated extracellular collagen concentration by regulating collagen gene expression was studied using pBSCA11 and pCAL2 probes containing insert sequences corresponding to the mRNAs for chicken$\alpha 1$(I) and $\alpha 2$(I) procollagen chains, respectively (FIG. 4) When hybridized with pBSCA11 (FIG. 4A), avian skin fibroblasts expressed two major bands of approximately 5.0 kb and 9.0 kb, whereas pCAL2 hybridized with a single band of approximately 5.2 kb (FIG. 4B). Incubation for 2 h with halofuginone ($10^{-9}$M) caused a 20% attenuation of collagen $\alpha 2$(I) gene expression without any change to collagen $\alpha 1$(I). After 24 h of incubation, a reduction of 32% and 40% was observed in the gene expression of $\alpha 2$(I) and $\alpha 1$(I), respectively.

Figure 5:
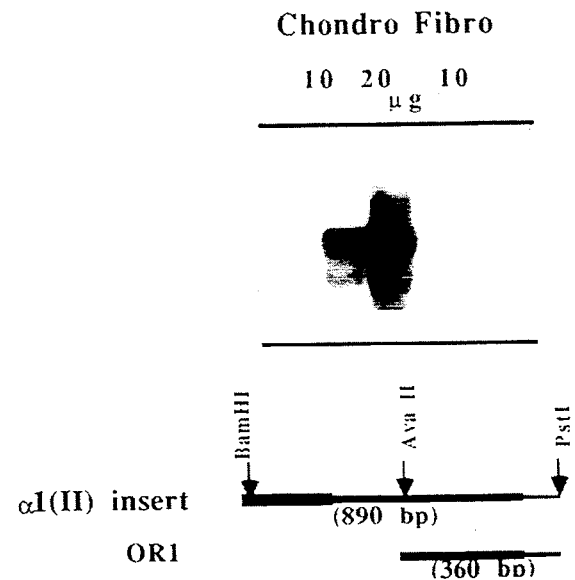
FIG. 5 shows the preparation of OR1, an avian collagen type II probe.

Effect of Halofuginone on Collagen Type I and II Gene Expression in Chondrocytes Avian chondrocytes were used in order to evaluate the specificity of halofuginone on the expression of various collagen genes. These cells, in their proliferative state in culture, express the genes for collagen types I and II. As a specific avian collagen type II probe, a fragment of 360 bp (AvaII/PstI) was used, designated OR1, which was derived from the 890 bp type II collagen genomic DNA fragment (BamHI/Pst/I) which share some similarity with collagen type $\alpha 1$(I) mRNA [H. D. Nah, et al., Collagen Rel. Res., Vol. 8, pp. 277-294 (1988)]. The probe OR1 hybridized with collagen type II in avian chondrocytes and not with collagen type I in avian skin fibroblasts (FIG. 5). Using the probes for chicken $\alpha 1$ and $\alpha 2$ procollagen type I chains and OR1 as a probe for collagen type II, it was demonstrated that in chondrocytes, halofuginone affects only collagen $\alpha 1$(I) gene expression without any inhibitory effect on either $\alpha 2$(I) or collagen type II gene expression (FIG. 6).

Effect of Halofuginone on Extracellular Collagen Degradation

Collagen degradation was evaluated in order to study the possibility that halofuginone, in addition to its effect on collagen synthesis, affects also collagen degradation. Avian skin fibroblasts were cultured for 24 h with or without $10^{-9}$M of halofuginone (a concentration which had previously caused maximal reduction in [$^3$H]proline incorporation to CDP) and the media were assayed for collagen degradation (Table 2). DMEM with 5% FCS did not contain any measurable collagen degradation activity since the same concentration of [$^3$H]CDP was found before and after 24 h of incubation. No significant difference in collagen degradation was observed in the media of the untreated cells, compared with cells treated with halofuginone.

TABLE 2

Effect of halofuginone on collagenase activity secreted by avian skin fibroblasts
Avian skin fibroblasts were incubated with halofuginone for 24 h. At the end of incubation, an aliquot of the medium was incubated for an additional 24 h with radiolabeled proteins prepared by incubating cells with 15 μCi/ml of [$^3$H]proline for 48 h.
At the end of the incubation, radiolabeled CDP and NCDP were determined. The results are the mean ± SE of four wells.

| Additive (M) | CDP (dpm) | Collagenase activity (%) |
|---|---|---|
| Medium (no cells) | 2699 ± 135 | 0 |
| None | 2288 ± 328 | 15.2 |
| Halofuginone $10^{-9}$ | 2152 ± 216 | 20.0 |

Conclusions

All cell cultures tested, primary cultures of avian and mouse skin fibroblasts, avian chondrocytes and the line Rat-1, synthesized and secreted collagen (collagenase-digestible proteins) under the given culture conditions. The ratio of [$^3$H]proline incorporation into collagenase-digestible and non-digestible proteins exported to the medium, was the lowest in the Rat-1 cell line, in agreement with other reports demonstrating a reduced collagen synthesis in chemically or virally transformed fibroblasts [A. Hatamochi, et al., *J. Invest. Dermatol.*, Vol. 96, pp. 473-477 (1991); B. H. Howard, et al., *J. Biol. Chem.*, Vol. 253, pp. 5869-5874 (1978); and V. E. Avedimento, et al., *Nucleic Acid Res.*, Vol. 9, pp. 1123-1131 (1981)].

Halofuginone caused dose-dependent inhibition in the CDP without affecting the secretion of other [$^3$H]proline-containing proteins (FIG. 2), suggesting that halofuginone is a specific inhibitor of collagen synthesis. The responsiveness of both fibroblasts and chondrocytes to the inhibitor shows that its effect is not tissue-specific. The response of both avian and mammalian cells suggests no species specificity. Furthermore, the Rat-1 cell line was more sensitive to halofuginone compared with the primary cultures: a concentration as low as $10^{-11}$M of the drug was sufficient to cause a 65% inhibition of exported radiolabeled collagen, compared with 20–30% in the primary cultures. The effect of halofuginone on collagen metabolism was not due to an effect on cell proliferation (Table 1) or to collagen degradation (Table 2).

Chondrocytes are known to synthesize five genetically-distinct collagen types, but in culture, avian chondrocytes also express the genes encoding for collagen types I and II. Fibroblasts synthesize two types of collagen, of which type I comprises approximately 85%, and most of the rest is collagen type III. Thus, all cell types used in this study including chondrocytes, expressed the genes encoding for collagen type I. By using type-specific collagen probes and cell cultures that express type I and type II collagen genes (FIGS. 4 and 6), it was demonstrated that halofuginone attenuated the expression of $\alpha1(I)$ gene expression without any inhibitory effect on the expression of $\alpha1(II)$ gene (a slight increase was even observed). These results suggest that the inhibitory effect of halofuginone on CDP production in growth-plate chondrocytes is due only to inhibition of type I collagen synthesis. No effect of halofuginone on $\alpha2(I)$ gene expression in growth-plate chondrocytes was observed.

In avian skin fibroblasts, halofuginone depressed the gene expression of both polypeptides of collagen type I but at different rates: that of $\alpha2(I)$ was affected as early as after 2 h, whereas an incubation period of 24 h was required to demonstrate any effect on $\alpha1(I)$ sub-unit (FIG. 4). The inhibition of the gene expression of the two polypeptides of type I collagen by halofuginone resulted in a decrease in their respective synthesis, as was demonstrated by immunoprecipitation with specific type I collagen antiserum (FIG. 3).

EXAMPLE 2

The effect of halofuginone on collagen synthesis and collagen $\alpha1$ (I) gene expression by skin fibroblasts taken from scleroderma and GVHD patients was evaluated. In addition, the mechanism by which halofuginone affects collagen metabolism was studied.

Materials and Methods

Materials

L-[2,3,4,5-$^3$H]proline (122 Ci/mmol) and ATP($\alpha$-$^{32}$P 6000 Ci/mmol) were obtained from The Radiochemical Centre (Amersham, U.K.). [$^{14}$C]chloramphenicol (40 mCi/mmol) was obtained from New England Nuclear (Boston, Mass., U.S.A.). Highly purified *Clostridium histolyticum* collagenase type VII free of non-specific proteinases, $\beta$-aminopropionitrile, Dulbecco's modified Eagle's medium (DMEM) and trypsin-EDTA solution (0.25%–0.02%) were obtained from Sigma (St. Louis, Mo., U.S.A.). Fetal calf serum (FCS) was obtained from Biochemical Industries (Bet HaEmek, Israel). Halofuginone bromhydrate (Stenorol) was obtained from Roussell (Paris, France).

Plasmids

A 4.0 Kb XbaI-SalI fragment of the human pro-$\alpha1(I)$ collagen plasmid [COL1A1; M. Chu, et al., *J. Biol. Chem.*, Vol. 260, pp. 2315-2320 (1985)] was used as a probe for Northern blot analysis. ColCAT3, the mouse $\alpha1(I)$ promoter extending from $-222$ to $+116$ bp driving the chloramphenicol acetyltransferase (CAT) gene [Rippe, et al., *Mol. Cell. Biol.*, Vol. 9, pp. 2224-2227 (1989)] was used in CAT assays. pRSVCAT containing the SV40 enhancer and promoter driving CAT was used as a positive control in CAT assays [Gorman, et al., *Mol. Cell. Biol.*, Vol. 2, pp. 456-467 (1982)].

Cells

Skin biopsies (3 mm) were taken from three chronic GVHD patients (aged 38–45) and a scleroderma patient, from the right subcapsular area, which were macroscopically and histopathologically involved with GVHD. The GVHD and scleroderma diagnosis was also confirmed by pathology. The normal skin biopsy was taken from a 42-year-old woman, who underwent plastic surgery. All biopsies were taken according to the guidelines established by the Hadassah University Hospital Experimentation Committee. Biopsies were put as explants, dermis down, in a 35 mm tissue culture dish in 1 ml EM (enriched medium based on DMEM with 10% inactivated FCS, 2 mM L-glutamine, 0.1% non-essential amino acids, 100 $\mu$g/ml penecillin and 100 $\mu$g/ml streptomycin) and incubated at 37° C. in a humidified atmosphere of 5% $CO_2$. Media were changed once a week until primary fibroblasts grew out of the explant and became confluent. For the experiments, fibroblasts (matched for passage number) were seeded in EM in 35 mm$^2$ petri dishes or in wells of multi-well cluster tissue culture plates. For the CAT assay, the mouse fibroblast NIH3T3 cells were used.

Transient Transfections and CAT Assay

Mouse fibroblast NIH3T3 cells were plated at a cell density of $8 \times 10^5$ cells/90 mm plate. The next day, 8 $\mu$g of pCOlCAT3 or pRSV plasmids were applied onto each dish by calcium-phosphate co-precipitation. Glycerol shock was performed 17 hr after transfection and the medium was replaced with a new medium containing various concentrations of halofuginone. Cells were harvested 24 hr later and extracts were prepared by freezing and thawing cell pellets in buffer containing 25 mM Tris, pH 7.8 and 25 mM EDTA. CAT activity was determined as described by Gorman, et al., [*Mol. Cell. Biol.*, Vol. 2, pp. 456-467 (1982)]. In brief, for each reaction, equal amounts of protein (200 $\mu$g) were incubated with 80 ng acetyl-CoA and 1 $\mu$l [$^{14}$C]chloramphenicol in 150 $\mu$l 25 mM Tris, pH 7.8 buffer. The reaction was carried out at 37° C. for 4 hr and terminated by ethyl-acetate extraction. Radiolabeled products were separated by thin-layer chromatography and visualized by autoradiography with Agfa X-ray films at room temperature for several days.

Evaluation of Collagen and Non-Collagen Protein Synthesis

Cells were incubated with various concentrations of halofuginone in 0.5 ml glutamine-free DMEM containing 5% FCS, ascorbic acid (50 $\mu$g/ml), $\beta$-aminopropionitrile (50 $\mu$g/ml) and 2 $\mu$Ci of [$^3$H]proline. At the end of incubation, the medium was decanted and incubated with or without collagenase for 18 h, followed by TCA precipitation. The amount of radiolabeled collagen was estimated as the difference between total [$^3$H]proline-containing proteins and those left after collagenase digestion [Pines, et al., *Bone and Mineral*, Vol. 9, pp. 23–33 (1990); Granot, et al., *Mol. Cell. Endocrinol.*, Vol. 80, pp. 1–9 (1991)].

RNA Isolation and Northern Blot Hybridization

Total RNA was isolated using the guanidinium-thiocyanate-phenol technique, as described by P. Chomczynski and N. Sacchi [*Anal. Biochem.*, Vol. 162, pp. 156–159 (1987)]. The RNA was subjected to 1% agarose denaturing gel electrophoresis, followed by blotting onto a nylon filter (GeneScreen Plus, New England Nuclear, Boston, Mass., U.S.A.). cDNA probes were labeled using the random primer procedure (A. P. Feinberg, et al., *Anal. Biochem.*, Vol. 132, pp. 6–13 (1983)] with a commercial kit (Boehringer), and hybridization was performed overnight at 40° C. in a solution containing 10% dextran sulfate, 1% sodium dodecyl sulfate (SDS), 1M NaCl, 40% formamid and 200 μg/ml denatured herring sperm DNA. The hybridization was followed by two 30-min washes in 2×SSC (1×SSC contains 0.15M NaCl and 0.015M sodium citrate)- 0.1% SDS, and two 20-min washes in 1×SSC-0.1% SDS. The filters were exposed to X-ray film (Agfa-Curix) at 70° C., using intensifying screens. The integrity and the amount of the RNA were monitored by hybridizing the same blots with a murine glyceraldehyde 3-phosphate dehydrogenase (GAPDH) cDNA-specific 1.3 kb probe.

Results

Effect of Halofuginone on Collagen α1(I) Gene Expression

Figure 7:
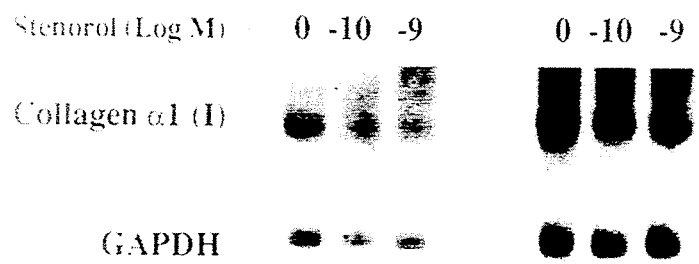
FIG. 7 Icompares the effect of halofuginone on collagen $\alpha 1$ (I) gene expression by skin fibroblasts of a healthy subject and a scleroderma patient.
Figure 8:
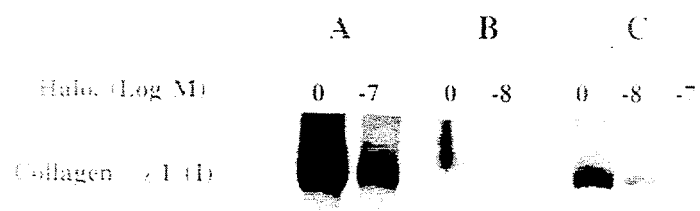
FIG. 8 shows the effect of halofuginone on collagen $\alpha 1$ (I) gene expression by skin fibroblasts of GVHD patients.

Cultures of skin fibroblasts from normal, scleroderma (FIG. 7) and three GVHD patients (FIG. 8) were prepared. After 24 h of incubation with various concentrations of halofuginone, total RNA was prepared and Northern blot analysis was performed, using a specific probe for human collagen α1(I). Collagen α1(I) gene expression was attenuated in response to halofuginone in all cultures tested. In normal and scleroderma patients, concentrations as low as $10^{-10}$M of halofuginone were sufficient to cause a significant reduction in the gene expression, and higher concentration of the drug further reduced the gene expression (FIG. 7). Cells derived from GVHD patients were less sensitive to halofuginone, and concentrations between $10^{-8}$M and $10^{-7}$M were needed to demonstrate significant reduction in collagen α1(I) gene expression (FIG. 8).

Effect of Halofuginone on Collagen Synthesis

Figure 9:
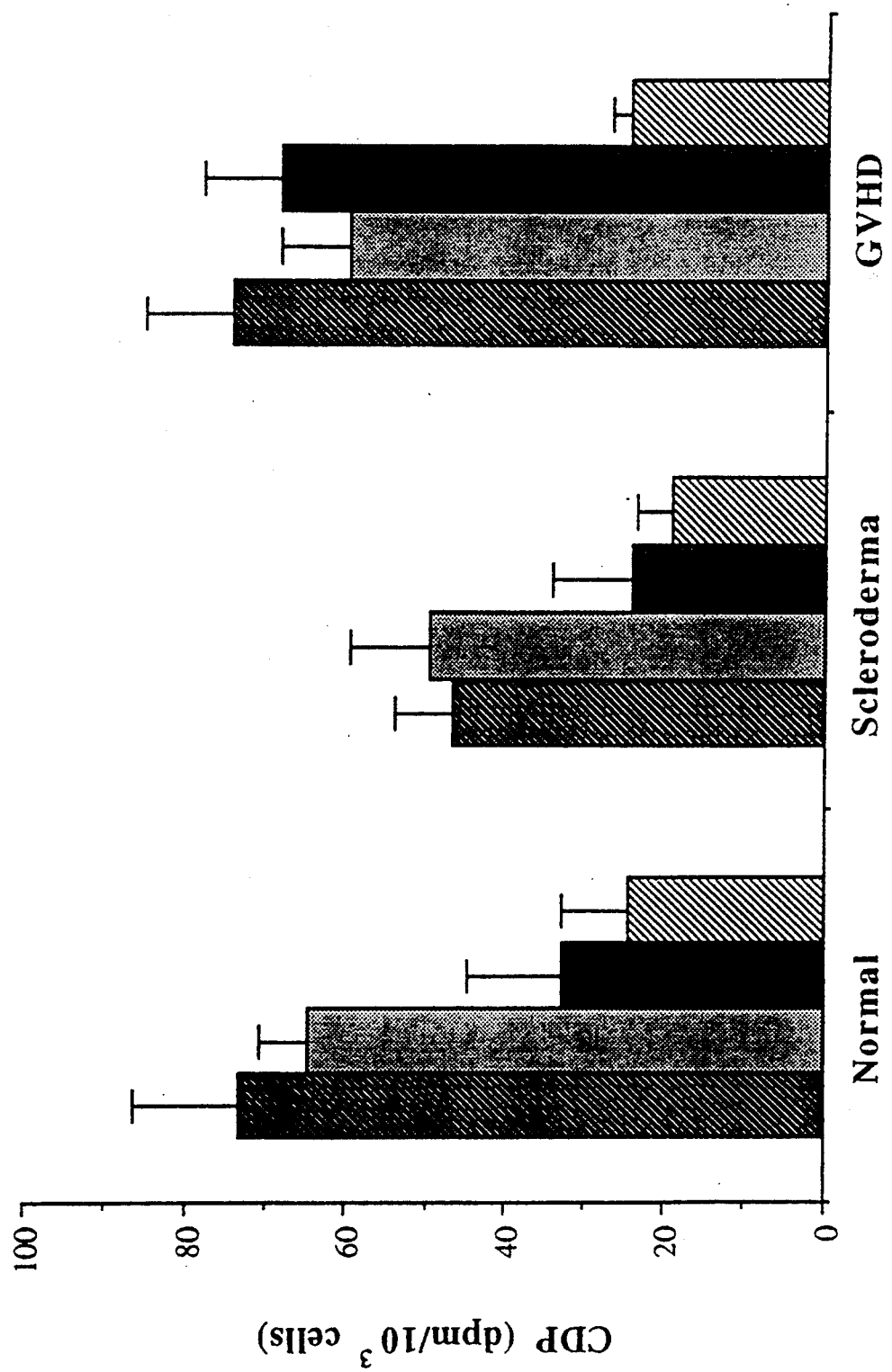
FIG. 9 graphically shows the effect of halofuginone on [$^3$H]proline incorporation to CDP exported by skin fibroblasts of a healthy subject and of scleroderma and GVHD patients.

Skin fibroblasts were incubated for 24 h in the presence of [$^3$H]proline exported radiolabeled proteins into the medium, of which 40% were collagenase-digestible (CDP) and the remaining were, by definition, non-digestible proteins (NCDP). Halofuginone inhibited in a dose-dependent manner the radiolabeled proline incorporation into CDP by skin fibroblasts derived from healthy individuals and scleroderma and GVHD patients (FIG. 9). Fibroblasts from the healthy individual were the most sensitive to the drug, compared to the fibroblasts either from scleroderma or GVHD patients, and decrease in [$^3$H]proline incorporation to CDP was observed in concentrations of $10^{-9}$M. Fibroblasts from GVHD patients were the least sensitive to the drug, and concentrations of $10^{-7}$M were needed in order to cause significant inhibition in [$^3$H]proline incorporation to CDP.

In addition to its effect on the basal levels of [$^3$H]proline incorporation to CDP, halofuginone also abrogated the TGF$\beta$-induced collagen synthesis by skin fibroblasts (Table 3). Incubation of skin fibroblasts with TGF$\beta$ for 24 h caused a dose-dependent induction of [$^3$H]proline incorporation to CDP, reaching 150% of the control levels when incubated with 3 ng/ml of TGF$\beta$. Halofuginone, at a concentration of $10^{-8}$M, inhibited [$^3$H]proline incorporation to CDP by 50%. When incubated together, halofuginone inhibited the TGF$\beta$-induced collagen synthesis.

TABLE 3

Effect of halofuginone on [$^3$H]proline incorporation to CDP in TGF$\beta$-induced cells Cells were incubated in the presence of [$^3$H]proline with TGFP$\beta$(1 and 3 ng/ml) or with Halo. ($10^{-8}$M) or in combination. After 24 h, the media were collected for determination of radiolabeled CDP. The results are the means ± SE of four wells. Means without a common superscript differ significanty (P<0.05) according to Duncan's multiple range test.

| Treatment | CDP (dpm × $10^5$ cells) |
|---|---|
| Control | 265.5 ± 10[b] |
| TGF$\beta$ 1 ng/ml | 288.8 ± 13[b] |
| TGF$\beta$ 3 ng/ml | 404.1 ± 9[a] |
| Halo. $10^{-8}$M | 116.7 ± 4[d] |
| TGF$\beta$ 1 ng/ml + Halo. $10^{-8}$M | 131.5 ± 4[d] |
| TGF$\beta$ 3 ng/ml + Halo. $10^{-8}$M | 166.9 ± 5[c] |

The Effect of Halofuginone on Collagen Synthesis Is Transient

Figure 10:
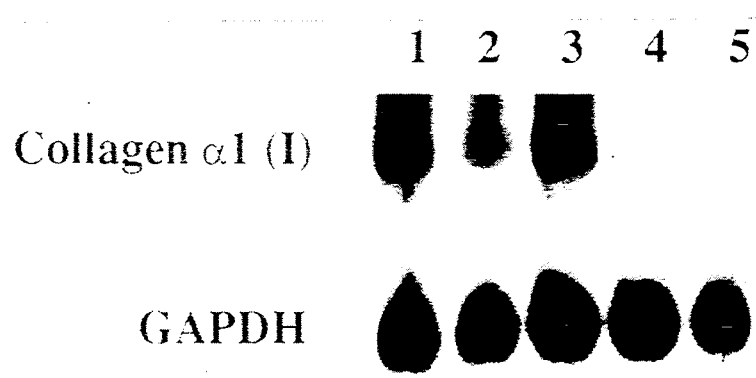
FIG. 10 shows the effect of halofuginone removal on collagen $\alpha 1$ (I) gene expression by skin fibroblasts of a GVHD patient.

Skin fibroblasts from a GVHD patient were incubated with or without $10^{-8}$M halofuginone for various time periods. RNA was prepared and hybridized with α1(I) collagen probe. Incubation of the cells with halofuginone for 72 h caused a marked reduction in collagen α1(I) gene expression (FIG. 10, lanes 1 and 2). Cells incubated only for the first 24 h in the presence of halofuginone and the rest, incubated 48 h without the drug, exhibited the same level of expression of the α1(I) collagen gene as the untreated cells (FIG. 10, lane 3). Addition of halofuginone to the cells for 24 h on the second or the third day of incubation, resulted in loss of the α1(I) collagen gene expression (FIG. 10, lanes 4 and 5).

Figure 11:
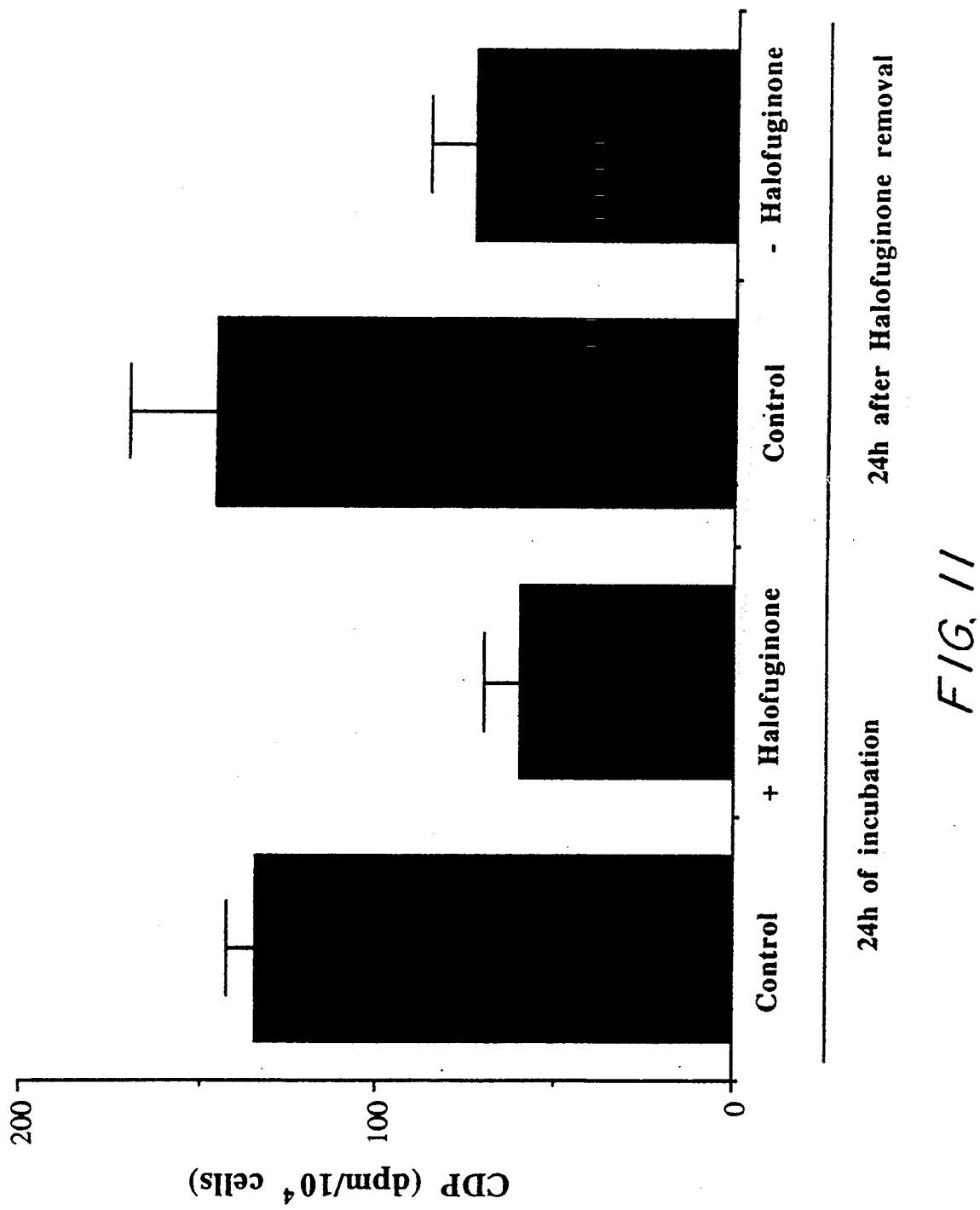
FIG. 11 graphically shows the effect of halofuginone removal on [$^3$H]proline incorporation to CDP exported by skin fibroblasts of a GVHD patient.

Cells were incubated with or without $10^{-7}$M halofuginone for 24 h, after which the media were replaced with fresh media without the drug (FIG. 11). The inhibitory effect of halofuginone on [$^3$H]proline incorporation to CDP by skin fibroblasts remained at the same level 24 h after removal of the drug.

Evaluation of Halofuginone Mode of Action

Two approaches were used in order to evaluate the mechanism by which halofuginone affects collagen α1(I) gene expression-DNA methylation and binding to the collagen α1(I) promoter.

Cells were incubated with $5 \times 10^{-6}$M 5-azacytidine, a potent inhibitor of DNA methyltransferase, or with halofuginone $10^{-9}$M, or in combination. After 24 h, [$^3$H]proline incorporation to CDP and NCDP was determined. 5-azacytidine, which by itself did not affect [$^3$H]proline incorporation to collagen and non-collagen proteins, also did not restore the halofuginone-dependent inhibition of collagen synthesis (Table 4).

TABLE 4

The effect of 5' azacytidine on halofuginone-dependent inhibition of [$^3$H]proline incorporation to CDP and NCDP Cells were incubated in the presence of [$^3$H]proline with 5'azaC ($5 \times 10^{-6}$M) or with Halo. ($10^{-9}$M) or in combination. After 24 h, the media were collected for determination of radiolabeled CDP. The results are the means ± SE of four wells. Means without a common superscript differ significantly (P<0.05) according to Duncan's multiple range test.

| Treatment | CDP | NCDP |
|---|---|---|
| | (dpm $\times$ 10$^5$ cells) | |
| Control | 1661 ± 198[a] | 2139 ± 293[a] |
| 5'azaC $5 \times 10^{-6}$M | 1606 ± 267[a] | 2010 ± 77[a] |
| Halo. $10^{-9}$M | 687 ± 104[b] | 2249 ± 114[a] |
| Halo. $10^{-9}$M + 5'azaC $5 \times 10^{-6}$M | 834 ± 129[b] | 2053 ± 97[a] |

Figure 12:
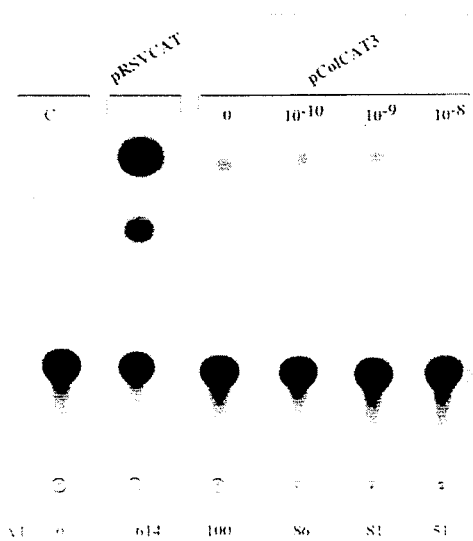
FIG. 12 shows CAT activity, presented as percent of halofuginone-untreated cells transfected with pCol-CAT3 as determined by densitometry.

The collagen α1(I) promoter encompasses regulatory elements which have a positive or negative contribution to the gene transcription. One of these regulatory sequences is located within the 222 base pairs upstream to the transcription start site and has a strong stimulatory effect on collagen α1(I) promoter [Rippe, et al., Mol. Cell. Biol., Vol. 9, pp. 2224-2227 (1989)]. The CAT assay was used in order to evaluate the effect of halofuginone on the stimulatory region of the collagen α1(I) promoter. The plasmid pColCAT3, which contains the enhancing region driving the CAT reporter gene, was transfected into mouse fibroblasts NIH3T3, and after a glycerol shock, cells were incubated with various concentrations of halofuginone for 24 hr. The CAT activity is presented as percent of halofuginone-untreated cells transfected with pColCAT3 as determined by densitometry (FIG. 12). It can be seen that halofuginone had a dose-response effect on collagen promoter activity. In the presence of $10^{-10}$M halofuginone, collagen promoter activity declined to 81%, and at concentration of $10^{-8}$M of the drug, a further reduction was observed, reaching approximately 50% of the promoter activity of the untreated cells. It should be noted that collagen promoter activity was relatively low when compared to the activity induced by the SV40 promoter in cells transfected with pRSVCAT, which served as a positive control for CAT activity.

Conclusions

In Example 1, we demonstrated that halofuginone inhibited collagen synthesis by avian and murine fibroblasts in culture. Moreover, using avian chondrocytes, which in culture expressed the genes coding for collagen type I and II, we could demonstrate that halofuginone specifically inhibited collagen type I gene expression. In fibroblasts, the drug mainly affects collagen α1(I) gene expression. In Example 2, we demonstrated that halofuginone inhibited, in a dose-dependent manner, collagen production (FIG. 9) and collagen α1(I) gene expression (FIGS. 7 and 8) by healthy human skin fibroblasts, and fibroblasts derived from scleroderma and GVHD patients, which usually display overproduction of collagen in the connective tissues. It was also demonstrated that halofuginone, in addition to its effect on the basal level of collagen synthesis, also inhibited the TGFβ-induced collagen synthesis (Table 3).

Although the inhibitory effect of halofuginone on collagen metabolism is not species-dependent, and the drug affected fibroblasts from mammalian and non-mammalian species, not all of them exhibited the same degree of sensitivity. Transformed cells were more sensitive to the drug than skin fibroblasts in primary culture, and higher levels of halofuginone were needed to demonstrate a significant effect on collagen gene expression (FIGS. 7 and 8) and [$^3$H]proline incorporation to CDP (FIG. 9) by fibroblasts derived from GVHD patients, compared to fibroblasts from healthy subjects. These data suggest that the cells may contain specific regulatory elements affecting halofuginone action on the collagen α1(I) gene. The effect of halofuginone on collagen α(I) gene expression (FIG. 10) and incorporation of [$^3$H]proline to CDP (FIG. 11) was transient, and the effect of the drug persisted 24–48 h after drug removal.

One mechanism that has been correlated with inhibition of collagen gene expression was DNA methylation. Loss of expression of collagen proα1(I) and proα2(I) genes was accompanied by hypermethylation of these genes in human SV40-transformed fibroblasts [Parker, et al, Nucleic Acid Res., Vol. 10, pp. 5879-5891 (1982)] and in vitro methylation of the promoter and enhancer of proα1(I) collagen gene led to its transcriptional inactivation [Thompson, et al., J. Biol. Chem., Vol. 266, p. 2549-2556 (1991)]. Treatment of cells with 5-azacytidine, a potent inhibitor of DNA methyltransferase, restored transcriptional activity of the collagen genes. 5-azacytidine did not affect the halofuginone-dependent inhibition of collagen synthesis (Table 4), suggesting that DNA methylation is not involved in the inhibition of collagen type I gene expression. Using ColCAT3, the mouse α1(I) promoter, we could demonstrate that halofuginone affects the regulatory sequences of the collagen type I promoter located within the 222 base pairs upstream to the transcription start site, which has a strong stimulatory effect on collagen α1(I) promoter [Rippe, et al., Mol. Cell. Biol., Vol. 9, pp. 2224-2227 (1989)].

In summary, it has been demonstrated that halofuginone inhibited collagen synthesis by affecting the regulatory sequences of the collagen type I promoter and causing inhibition of the collagen α1(I) gene. The need for extremely low concentrations of halofuginone to inhibit collagen type I synthesis at transcriptional level, regardless of the tissue or animal species, and the fact that the drug exerts its effect on skin collagen content at concentrations which do not affect growth, indicate that halofuginone is a promising anti-fibrotic drug.

EXAMPLE 3

The effect of halofuginone on skin collagen content in the murine chronic type of GVHD was evaluated.

Materials and Methods

Materials

Hydroxy-L-proline, chloramin-T, and p-dimethyl aminobenzaldehyde were obtained from Sigma (St. Louis, Mo., U.S.A.). Rabbit anti-mouse collagen type I polyclonal antiserum (AB765) was obtained from Chemicon International,. Inc., Temecula, Calif., U.S.A.

cGVHD Induction

To induce chronic GVHD, spleen cells ($\approx 25.10^6$) from B10.D2 mice were injected i.v. into BALB/c mice, which received 600r $^{60}$Cobalt [H. N. Claman, et al., J. Invest. Dermatol., Vol. 84, p. 246 (1985)]. After cell transfer, mice were maintained in laminar flow hoods and received tetracycline water (250 mg/L) for 2 weeks. The control BALB/c mice, which were similarly irradiated and given BALB/c spleen cells, were treated similarly.

Skin Collagen Determination

Skin biopsies were hydrolyzed for 22 h at 110° C. with 6N HCl. Nitrogen was determined after Kjeldahl digestion by the spectrophotometric procedure, using an autoanalyzer as described by Krom (1980). The collagen-unique amino acid hydroxyproline was determined, as described by Dabev and Struck [*Biochem. Med.*, Vol. 5, p. 17 (1971)].

Preparation of Skin Sections

Mice skin samples were collected into phosphate buffered saline (PBS) and fixed overnight in 4% paraformaldehyde in PBS at 4° C. Serial 5 mm sections were prepared after the samples had been dehydrated in graded ethanol solutions, cleared in chloroform and embedded in Paraplast. The sections were deparafinized in xylene, rehydrated through a graded series of graded ethanol solutions, rinsed in distilled water (5 min), and incubated in 2×SSC at 70° C. for 30 min. The sections were then rinsed in distilled water and treated with pronase (0.125 mg/ml in 50 mM Tris-HCl, 5 mM EDTA, pH 7.5) for 10 min. After digestion, slides were rinsed in distilled water, postfixed in 10% formalin in PBS, blocked in 0.2% glycine, rinsed in distilled water, rapidly dehydrated through graded ethanol solutions, air-dried for several hours, and stained by hematoxylin-eosin.

Results

Effect of Halofuginone on BALB/c Skin Collagen Content

Figure 13:
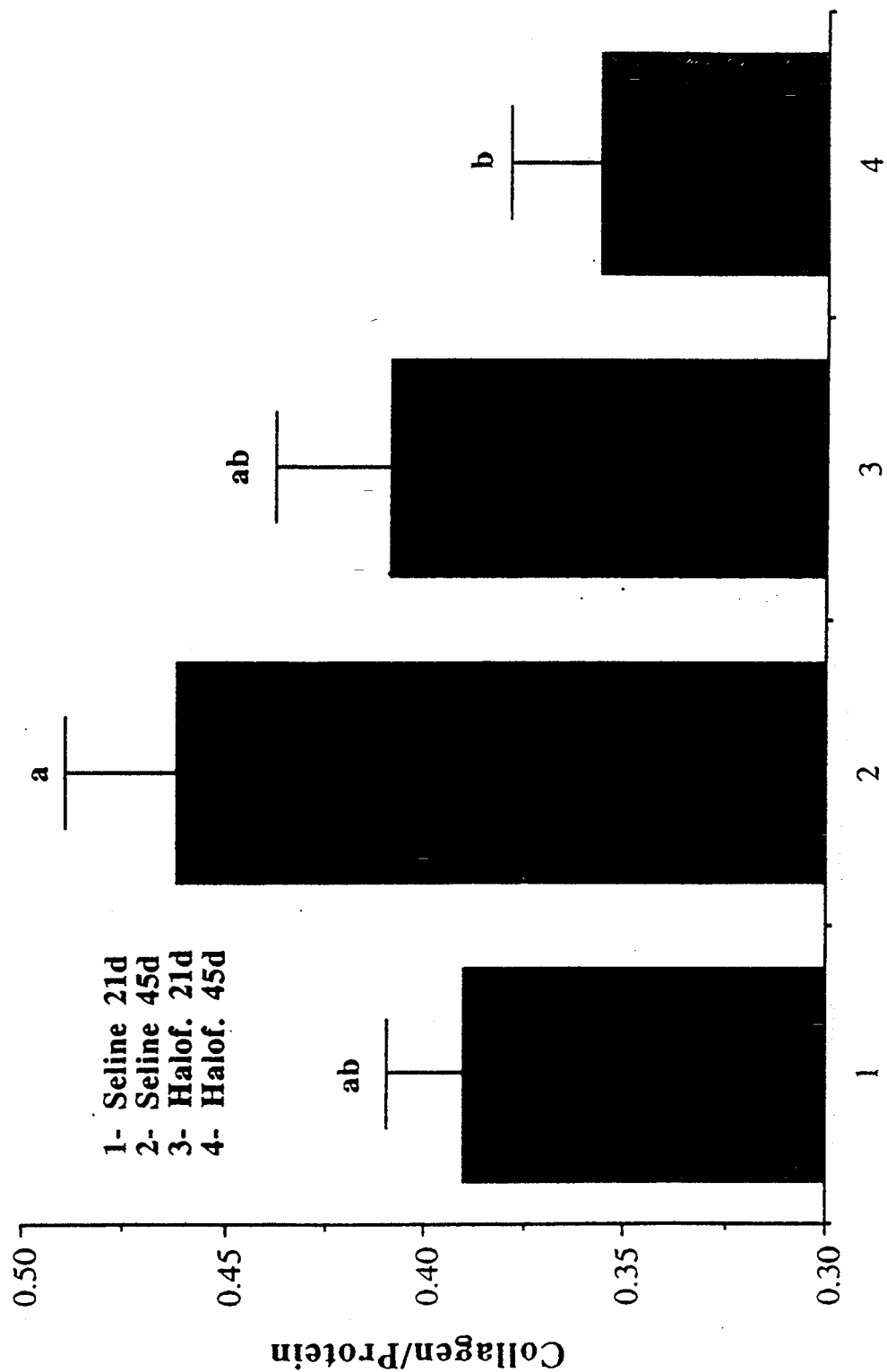
FIG. 13 graphically shows collagen content analysis of breast skin samples taken from mice treated with halofuginone for 21 days, 45 days, and controls.

Mice (BALB/c) were injected i.p. with saline or with 1 μg/mouse/day of halofuginone. After 21 and 45 days of treatment, breast skin samples were taken for collagen content determination (FIG. 13). After 21 days of treatment, no changes in skin collagen were observed. Daily injections of halofuginone for 45 days caused a significant reduction in skin collagen content, compared to the saline-injected mice. The dose of 1 μg/mouse/day was used in the subsequent experiments.

Effect of Halofuginone on Skin Collagen Conent in Chronic GVHD Mice

Chronic GVHD was induced by injecting spleen cells from B10.D2 mice to cobalt-radiated BALB/c mice. Three days before spleen cell transplantation and through all the experiment, mice were injected daily (i.p.) with 1 μg/mouse/day of halofuginone. The control BALB/c mice, transplanted with BALB/c spleen cells, were injected with the same dose of halofuginone. Every few days, the body weight was recorded, and at 45 and 52 days after transplantation, breast skin samples were taken for collagen content determination and for histology.

Figure 14A:
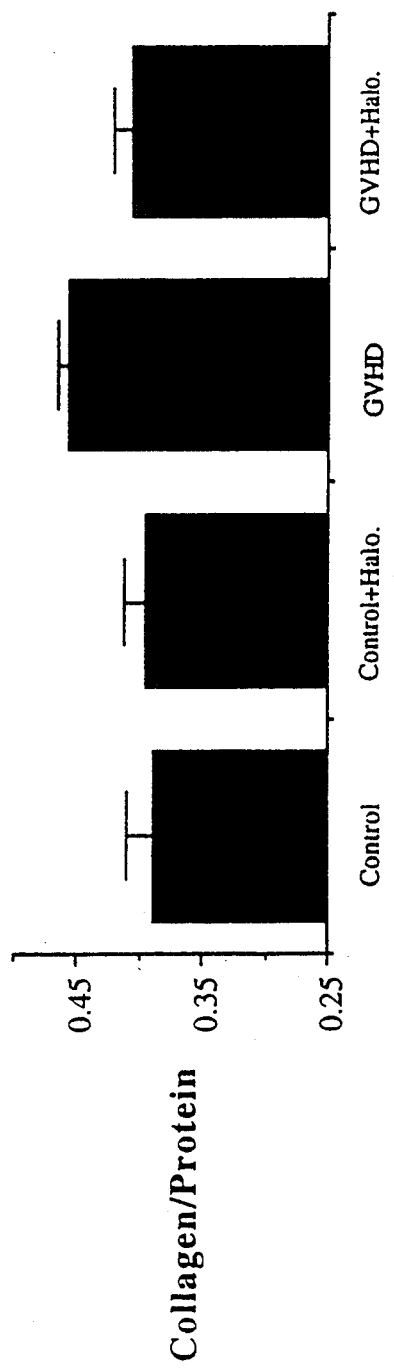
FIG. 14 graphically shows the effect of halofuginone on skin collagen content of mice after 45 and 52 days.
Figure 14B:
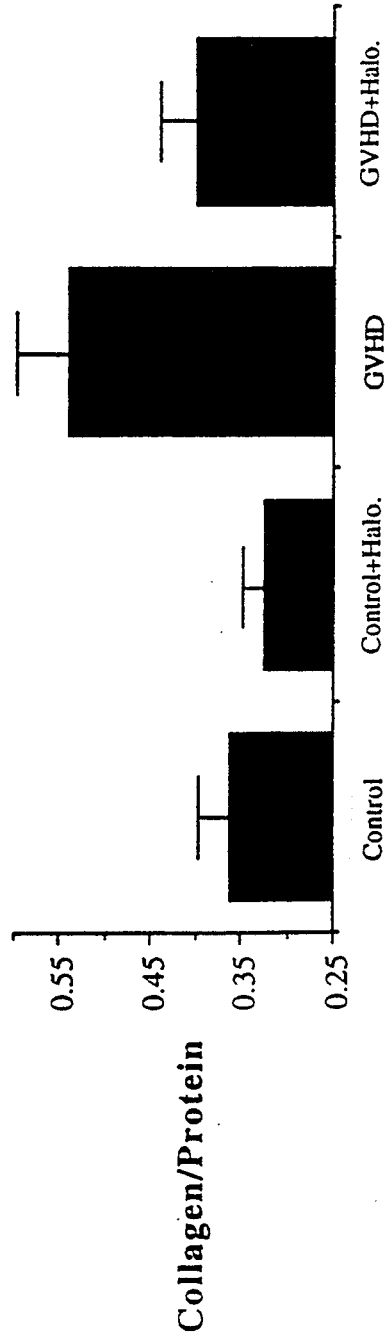

The skin collagen content, 45 days after spleen cell transplantation, was higher in the GVHD mice compared to the BALB/c controls (FIG. 14A). Halofuginone treatment caused a significant reduction in skin collagen content of the chronic GVHD mice, without affecting the collagen content of the control mice. At day 52, the skin collagen content of the BALB/c control mice had not changed, whereas an increase in collagen content was observed in the chronic GVHD mice skin (FIG. 14B). At this stage, halofuginone attenuated skin collagen, both in the control mice and the ones afflicted with GVHD.

Effect of Halofuginone on Body Weight

Figure 15:
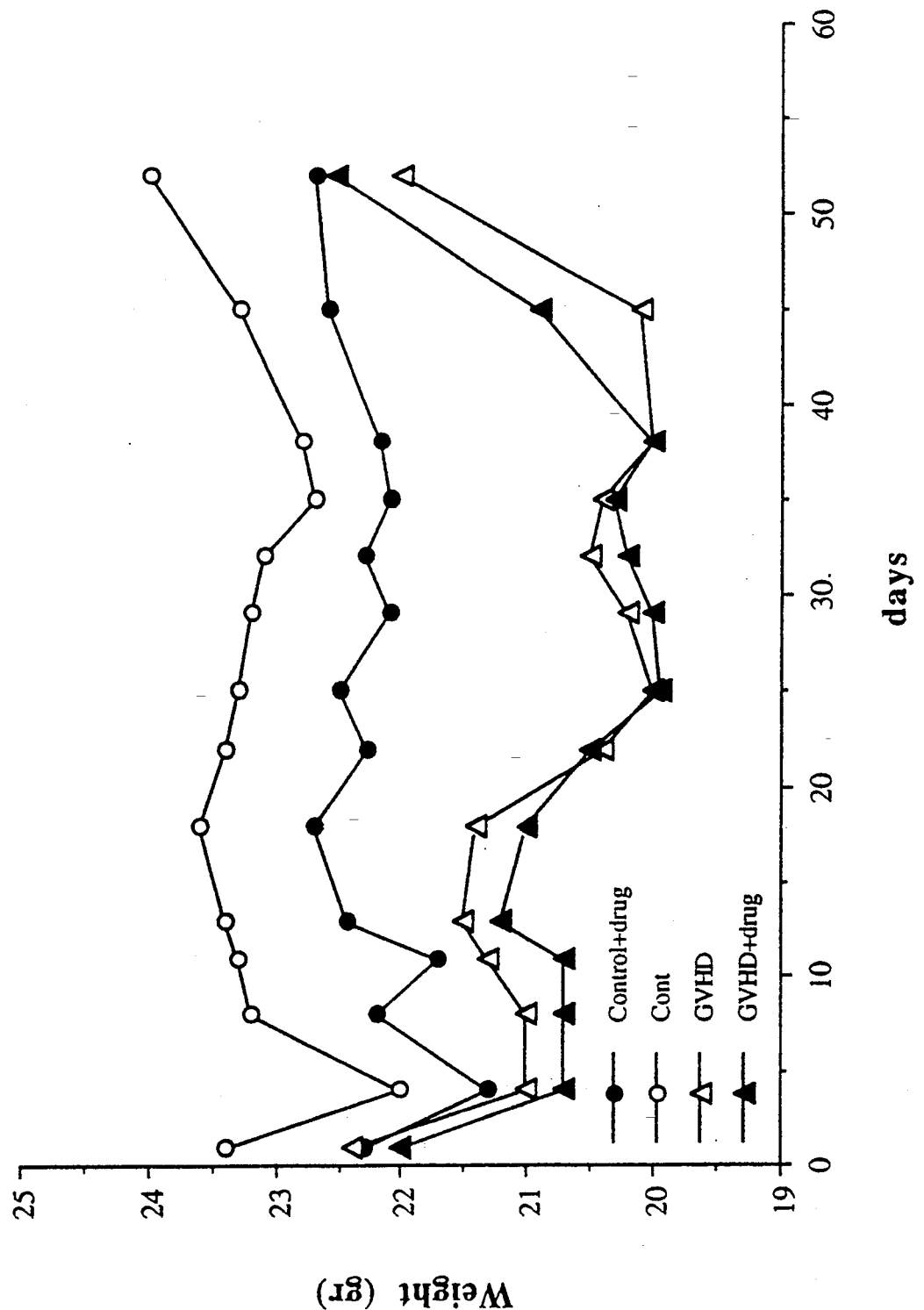
FIG. 15 graphically shows the effect of halofuginone on the body weight of control and GVHD mice.

Spleen cells transplantion caused reduction in body weight, both in GVHD and control mice (FIG. 15). Ten days after transplantation, the body weight of the control mice returned to the level of before the transplantation, whereas the body weight of the GVHD mice remained low, and reached the control weight only after 50 days. In both groups, no significant effect of halofuginone on body weight was observed.

Effect of Halofuginone on Skin Morphology

Spleen cell transplantation and development of chronic GVHD in BALB/c mice was associated with increase in skin fibrosis and total disappearance of the subcutaneous fat tissue (FIG. 16, A and C). Skin fibrosis was dramatically reduced in the skin section of the GVHD mouse injected daily with 1 μg of halofuginone (FIG. 16D). In addition, only a slight reduction in the subcutaneous fat tissue was observed in the treated mice, compared to the untreated ones (FIG. 16D). No changes in skin morphology were observed in the BALB/c control mice treated with halofuginone (FIG. 16B). Skin of GVHD mice contained higher levels of collagen type I compared to the control mice, as was demonstrated by immunohistochemistry using specific anti-mouse collagen type I antibodies (FIG. 16, E and G). Treatment with halofuginone caused reduction in skin collagen content of both GVHD and control mice (FIG. 16, F and H).

Effect of Halofuginone Dose and Injection Regime on Skin Collagen Content

Mice afflicted with chronic GVHD were injected i.p. with 0.2 or 1 μg/mouse halofuginone daily or every second day. BALB/c mice transplanted with BALB/c spleen cells served as controls. After 30 and 45 days, the mice were sacrificed, and skin samples from the breast area were taken for collagen determination. As shown in Table 5, 30 days after spleen cell transplantation, skin collagen content was higher in the GVHD mice, compared to the controls. The difference in skin collagen content between the GVHD and the control mice was no longer apparent after 45 days. In skin samples of GVHD mice injected daily with 0.2 or 1 μg/mouse and collected after 30 and 45 days, a significant reduction in collagen content, expressed either as percentage of total skin proteins or skin sample weight, was observed. Although skin collagen content of the control mice was also reduced after halofuginone treatment, the effect was not statistically significant (except after 30 days, when expressed as collagen/protein). Halofuginone injection every second day caused a greater reduction in skin collagen content, both in the control and GVHD mice.

TABLE 5

Effect of halofuginone on skin collagen content in control and GVHD mice.
Mice were injected i.p with 0.2 μg or 1 μg halofuginone per mouse or with tsaline alone daily or every second day. After 30 and 45 days of treatment, the mice were sacrificed and breast skin samples were taken for collagen determination. Results are expressed as collagen/total skin proteins or per sample weight, are the mean ± SE of 5 mice in each group. Means without a common superscript within a column, differ significantly ($P<0.05$) according to Duncan's multiple range test.

| Treatment | 30 days Collagen/Protein | 45 days Collagen/Protein | 30 days Collagen/Weight | 45 days Collagen/Weight |
|---|---|---|---|---|
| BALB/c/BALB/c | $0.576 \pm 0.021^{ab}$ | $0.602 \pm 0.071^{a}$ | $0.100 \pm 0.004^{b}$ | $0.103 \pm 0.01^{ab}$ |
| B10.D2/BALB/c (GVHD) | $0.611 \pm 0.021^{a}$ | $0.593 \pm 0.043^{ab}$ | $0.128 \pm 0.009^{a}$ | $0.106 \pm 0.02^{a}$ |

TABLE 5-continued

Effect of halofuginone on skin collagen content in control and GVHD mice.
Mice were injected i.p with 0.2 μg or 1 μg halofuginone per mouse or with tsaline alone daily or every second day. After 30 and 45 days of treatment, the mice were sacrificed and breast skin samples were taken for collagen determination. Results are expressed as collagen/total skin proteins or per sample weight, are the mean ± SE of 5 mice in each group. Means without a common superscript within a column, differ significantly (P<0.05) according to Duncan's multiple range test.

| Treatment | 30 days Collagen/Protein | 45 days Collagen/Protein | 30 days Collagen/Weight | 45 days Collagen/Weight |
|---|---|---|---|---|
| BALB/c/BALB/c + 0.2 μg/day Halo. | $0.504 \pm 0.047^b$ | $0.485 \pm 0.019^{abc}$ | $0.077 \pm 0.013^{bc}$ | $0.070 \pm 0.01^b$ |
| B10.D2/BALB/c (GVHD) + 0.2 μg/day Halo. | $0.468 \pm 0.018^b$ | $0.516 \pm 0.034^{abc}$ | $0.083 \pm 0.006^{bc}$ | $0.074 \pm 0.05^b$ |
| BALB/c/BALB/C + 1 μg/day Halo. | $0.517 \pm 0.036^{ab}$ | $0.563 \pm 0.017^{ab}$ | $0.072 \pm 0.007^c$ | $0.073 \pm 0.01^b$ |
| B10.D2/BALB/c (GVHD) + 1 μg/day Halo. | $0.454 \pm 0.017^b$ | $0.468 \pm 0.037^{bc}$ | $0.078 \pm 0.05^{bc}$ | $0.070 \pm 0.06^b$ |
| BALB/c/BALB/c + 1 μg Halo. every 2 day | $0.430 \pm 0.033^b$ | $0.391 \pm 0.026^c$ | $0.056 \pm 0.04^c$ | $0.057 \pm 0.02^c$ |
| B10.D2/BALB/c (GVHD) + 1 μg/Halo. every 2 day | $0.454 \pm 0.037^b$ | $0.397 \pm 0.037^c$ | $0.073 \pm 0.08^c$ | $0.064 \pm 0.03^c$ |

Conclusions

Fibrotic disorders, such as systemic sclerosis, GVHD, pulmonary and hepatic fibrosis, are distinguished by excessive production of connective tissue, resulting in destruction of normal tissue architecture and function. These diseases can best be interpreted in terms of perturbations in cellular functions, a major manifestation of which is excessive collagen deposition. In Example 3, the effect of halofuginone on skin morphology and collagen content in chronic GVHD mice was evaluated. These mice, which were used as an animal model of scleroderma, exhibited a high skin collagen content (Table 5). Halofuginone, which has been found to reduce collagen synthesis by skin fibroblasts derived from scleroderma and GVHD patients, also reduced skin collagen content in normal and chronic GVHD mice (FIGS. 13 and 14; Table 5). An administration regime, in which the drug was injected every second day, was found to be superior in reduction of skin collagen content, compared to daily injections (Table 5). These results are in agreement with previous observations, demonstrating that inhibition of collagen synthesis and collagen type I gene expression by halofuginone persisted 48 h after drug removal.

The reduction in skin collagen after halofuginone treatment was not accompanied by changes in body weight, in both control and chronic GVHD mice (FIG. 15). This confirms our previous study, which demonstrated that chickens fed diets supplemented with halofuginone for 7 weeks, starting immediately after hatching, exhibited a dose-dependent decrease in skin collagen content without any changes in feed efficiency or body weight [Granot, et al., Poult. Sci., Vol. 70, p. 1559 (1991)]. These results suggest that halofuginone affects mainly skin type I collagen synthesis, without affecting other collagen type I-containing tissues, such as bones. The expression of type I collagen genes follows a specific, discrete and tissue-specific pattern, and cell-specific transcriptional factors were suggested to regulated the collagen type I genes [Slack, et al., Mol. Cell Biol, Vol. 11 , p. 2066 (1991); Goldberg, et al., J. Biol. Chem., Vol. 267, p. 1962 (1992)]. For example, a specific sequence was found within the proα2(I) collagen promoter which, in transgenic mice, showed preferential activity in tail and skin, with a low activity in bone [Niederreither, et al., J. Cell. Biol., Vol. 119, p. 1361 (1992)]. Halofuginone was found to inhibit collagen α1(I) gene expression, by affecting the regulatory sequences of the collagen type I promoter located within the 222 base pairs upstresm of the transcription start site. This may suggest a tissue-specific regulatory sequence in this region of collagen α1(I) promoter.

On the morphological level, halofuginone decreased the fibrosis by decreasing collagen type I synthesis, and prevented the disappearance of the subcutaneous fat tissue, all of which are characteristic of the mice afflicted with chronic GVHD (FIG. 16).

Halofuginone fulfills the criteria of being an antifibrotic drug. Extremely low concentrations of halofuginone are needed to inhibit collagen type I synthesis at transcriptional level, regardless of the tissue or animal species. The drug exerts its effect on skin collagen content at concentrations which do not affect body growth. In addition, concentration of halofuginone can be found which, when injected, will inhibit only overproduction of collagen type I synthesis without affecting the normal collagen synthesis (Table 3).

It will be evident to those skilled in the art that the invention is not limited to the details of the foregoing illustrative examples and embodiments and that the present invention may be embodied in other specific forms without departing from the spirit or essential attributes thereof. The present examples and embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for the treatment of a fibrotic conditioning human patient suffering there from, comprising administering to the patient a composition comprising a pharmaceutically effective amount of a pharmaceutically active compound of formula I:

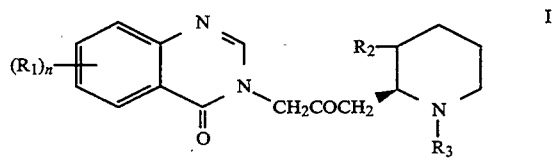

wherein:

n = 1 or 2

$R_1$ is a member of the group consisting of hydrogen, halogen, nitro, benzo, lower alkyl, phenyl and lower alkoxy;

$R_2$ is a member of the group consisting of hydroxy, acetocy, and lower alkoxy, and $R_3$ is a member of the group consisting of hydrogen and lower alkenoxy-carbonyl; effective to inhibit collagen type I synthesis.

2. A method according to claim 1, wherein said fibrotic condition is scleroderma.

3. A method according to claim 1, wherein said fibrotic condition is graft-versus-host disease (GVHD).

4. The method of claim 2 wherein the pharmaceutically active compound is halofuginone.

5. The method of claim 3 wherein the pharmaceutically active compound is halofuginone.

6. A method for treating a disease state associated with excessive collagen deposition in a human patient comprising administering to said patient a pharmaceutically effective amount of an α1 type I collagen synthesis inhibitor wherein said inhibitor is halofuginone.

* * * * *